(12) United States Patent
Sharma et al.

(10) Patent No.: US 9,267,783 B1
(45) Date of Patent: Feb. 23, 2016

(54) SPLIT INTEGRATION MODE ACQUISITION FOR OPTIMIZED OCT IMAGING AT MULTIPLE SPEEDS

(71) Applicant: Carl Zeiss Meditec, Inc., Dublin, CA (US)

(72) Inventors: Utkarsh Sharma, Dublin, CA (US); Matthew J. Everett, Livermore, CA (US); Muhammad K. Al-Qaisi, Dublin, CA (US); Hueyming Tzeng, San Jose, CA (US); Xing Wei, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 14/482,988

(22) Filed: Sep. 10, 2014

(51) Int. Cl.
*G01B 9/02* (2006.01)
*A61B 3/10* (2006.01)
*G01N 21/17* (2006.01)

(52) U.S. Cl.
CPC ............ *G01B 9/02044* (2013.01); *A61B 3/102* (2013.01); *G01B 9/02083* (2013.01); *G01B 9/02091* (2013.01); *G01N 2021/1787* (2013.01)

(58) Field of Classification Search
CPC ........... G01B 9/02091; G01B 9/02044; G01B 9/02083; A61B 5/0066; A61B 5/0073; A61B 3/102; G01N 21/4795; G01N 2021/1787; G01J 3/45
See application file for complete search history.

(56) References Cited

U.S. PATENT DOCUMENTS

| 8,500,279 | B2 | 8/2013 | Everett et al. |
| 8,504,141 | B2 | 8/2013 | Suehira et al. |
| 2010/0110376 | A1* | 5/2010 | Everett .................. A61B 3/102 351/206 |
| 2013/0120757 | A1 | 5/2013 | Yu et al. |
| 2013/0271772 | A1* | 10/2013 | Johnson ............. G01B 9/02004 356/479 |
| 2013/0301000 | A1* | 11/2013 | Sharma .................. A61B 3/102 351/206 |

FOREIGN PATENT DOCUMENTS

WO   2013/154953 A1   10/2013

OTHER PUBLICATIONS

B. PovaZay, B. Hofer, B. Hermann, C. Torti, V. Kajic A. Unterhuber, W. Drexle, High-Speed High-Resolution Optical Coherence Tomography at 800and1060 nm, Dec. 30, 2008, Proc. SPIE 7139, 1st Canterbury Workshop on Optical Coherence Tomography and Adaptive Optics, 71390R; doi:10.1117/12.817399.*
Bernhard Baumann, WooJhon Choi, Benjamin Potsaid, David Huang,Jay S. Duker, and James G. Fujimoto, Swept source / Fourier domain polarization sensitive optical coherence tomography with a passive polarization delay unit, Apr. 23, 2012, Optics Express, vol. 20, No. 9, p. 10218-10230.*
Huang et al., "Optical Coherence Tomography", Science, vol. 254, Nov. 22, 1991, pp. 1178-1181.
(Continued)

*Primary Examiner* — Michael A Lyons
*Assistant Examiner* — Violeta A Prieto
(74) *Attorney, Agent, or Firm* — Morrison & Foerster LLP

(57) ABSTRACT

Split Integration Mode (SIM) acquisition schemes are presented that enable optical coherence tomography (OCT) imaging at multiple rates. SIM enables a system and method of operation having a first mode and a second mode, wherein the fundamental acquisition rate of the detector is the same in the two modes, but wherein the generated signals in the second mode are digitally combined prior to signal processing to create a data set with an effective acquisition rate less than the fundamental acquisition rate.

15 Claims, 3 Drawing Sheets

(56) References Cited

OTHER PUBLICATIONS

Lee et al., "In vivo Optical Frequency Domain Imaging of Human Retina and Choroid", Optics Express, vol. 14, No. 10, May 15, 2006, pp. 4403-4411.
Leitgeb et al., "Performance of Fourier Domain vs. Time Domain Optical Coherence Tomography", Optics Express vol. 11, No. 8, Apr. 21, 2003, pp. 889-894.
Leitgeb et al., "Ultrahigh Resolution Fourier Domain Optical Coherence Tomography", Optics Express, vol. 12, No. 10, May 17, 2004, pp. 2156-2165.
Nassif et al., "In Vivo High-Resolution Video-Rate Spectral-Domain Optical Coherence Tomography of the Human Retina and Optic Nerve", Optics Express, vol. 12, No. 3, Feb. 9, 2004, pp. 367-376.
Nidek, "Optical Coherence Tomography RS-3000 Advance", Nidek Co., Ltd., Available at <http://www.nidekintl.com/products/diagnosis/rs-3000advance.html>, Oct. 25, 2013, 5 pages.
Potsaid et al., "MEMS Tunable VCSEL Light Source for Ultrahigh Speed 60kHz—1MHz Axial Scan Rate and Long Range Centimeter Class OCT Imaging", Proc. of SPIE, vol. 8213, 2012, pp. 82130M-1-82130M-8.
Potsaid et al., "Ultrahigh Speed Spectral / Fourier Domain OCT Ophthalmic Imaging at 70,000 to 312,500 Axial Scans per Second", Optics Express, vol. 16, No. 19, Sep. 15, 2008, pp. 15149-15169.
Wojtkowski et al., "Three-Dimensional Retinal Imaging with High-Speed Ultrahigh-Resolution Optical Coherence Tomography", Ophthalmology, vol. 112, No. 10, Oct. 2005, pp. 1734-1746.
Yun et al., "Motion Artifacts in Optical Coherence Tomography with Frequency-Domain Ranging", Optics Express, vol. 12, No. 13, Jun. 28, 2004, pp. 2977-2998.

* cited by examiner

SPLIT INTEGRATION MODE ACQUISITION FOR OPTIMIZED OCT IMAGING AT MULTIPLE SPEEDS

TECHNICAL FIELD

The present application relates to the field of Optical Coherence Tomography, in particular a system and mode of operation that allows for optimized OCT imaging at multiple speeds.

BACKGROUND

Optical Coherence Tomography (OCT) is a technique for performing high-resolution cross-sectional imaging that can provide images of tissue structure on the micron scale in real time (Huang et al. "Optical Coherence Tomography" Science 254(5035):1178 1991). OCT is a method of interferometry that determines the scattering profile of a sample along the OCT beam. Each scattering profile is called an axial scan, or A-scan. Cross-sectional images (B-scans), and by extension 3D volumes, are built up from many A-scans, with the OCT beam moved to a set of transverse locations on the sample. OCT provides a mechanism for micrometer resolution measurements.

It has been demonstrated that frequency-domain OCT (FD-OCT) has advantages over the original time-domain OCT (TD-OCT) (see for example R. Leitgeb, C. K. Hitzenberger, and A. F. Fercher, "Performance of Fourier domain vs time domain optical coherence tomography," Optics Express, 11, pp 889-894 (2003)). FD-OCT methods use the fact that interference between light scattered from the sample and the reference beams causes spectral interference fringes, or modulation in the intensity of the combined beam as a function of optical frequency. The spacing of the interference fringes depends on the difference in optical group delay between the light scattered from the sample and the reference light. In FD-OCT the optical path length difference between the sample and reference arms is not mechanically scanned. A full A-scan can be obtained in parallel for all points along the sample axial line within a short time, typically determined by the wavelength sweep rate of a swept source in swept-source OCT (SS-OCT) or the line scan rate of the line scan camera in spectral-domain OCT (SD-OCT). In SD-OCT, a grating, a prism, or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum. Typically the light source emits a broad range of optical frequencies simultaneously. In SS-OCT, a laser source is rapidly tuned through a range of wavelengths encoding the spectral information in time.

While FD-OCT (SD-OCT and SS-OCT) has already demonstrated tremendous improvement in acquisition speed over time-domain OCT, there are still many advantages of further increasing the speed of OCT systems. Many applications can benefit from denser sampling, resulting in finer details and higher resolution. At the same time, faster acquisition also helps to reduce motion artifacts. In ophthalmic OCT, increased data acquisition rate could be used to acquire higher density and wider field of view (FOV) cube data. Multi-frame averaging could result in speckle suppression and improved clarity in visualizing layered structure of the retina. Functional extensions of OCT such as OCT angiography could also benefit from high acquisition speeds as these techniques typically require repeated measurements and are susceptible to motion of the eye.

However, an increase in speed comes at the cost of sensitivity of the OCT system, if the optical power on the sample remains unchanged. In ophthalmic OCT systems, the incident power on the eye cannot exceed safe exposure limits as determined by laser and safety standards. Hence, while faster acquisition systems can obtain denser data sets, or make measurements more immune to motion artifacts, the sensitivity decreases. Therefore, high-sensitivity in vivo imaging is more challenging at higher speeds. High-sensitivity, however, is critical for several OCT imaging applications, for example, visualization of structures with typically low SNR including but not limited to the vitreous and the choroid. One commercial ophthalmic OCT system from Nidek, the RS-3000 Advance, advertises a user selectable OCT sensitivity option in which the system can acquire images in one of three sensitivities: ultra fine, fine, and regular trading off scan speed and sensitivity based on ocular pathology (http://www.nidek-intl.com/products/diagnosis/rs-3000advance.html).

Several research studies have looked into exploring the performance of OCT systems at various acquisition speeds. Benjamin Potsaid et al. explored the trade-offs between system acquisition speed and sensitivity performance of the system for ophthalmic imaging (B. Potsaid et al., "Ultrahigh Speed Spectral/Fourier domain OCT Ophthalmic Imaging at 70,000 to 312,500 axial scans per second," Optics Express, 16 (19), pp 15149-15169 (2008)). Potsaid et al. built four different OCT system configurations each operating at a different speed. Applying this approach to commercial systems would greatly impact system size and cost. In a later study, Potsaid et al. demonstrated a MEMS tunable VCSEL light source with sweep rates changing from 60 kHz to 1 MHz (B. Potsaid et al., "MEMS tunable VCSEL light source for ultrahigh speed 60 kHz-1 MHz axial scan rate and long range centimeter class OCT imaging," SPIE Proceedings, 8213, 82130M-1 (2012)). However, this is not a preferred solution as it is challenging to maintain similar spectral characteristics of the light source at different speeds, and special design or calibration efforts are needed. In this design, a booster semiconductor optical amplifier was used to approximately maintain similar bandwidth at different speeds. However, such a solution would add to the cost of the laser.

Johnson at al. also proposed multi-speed operation using an SS-OCT system (WO Publication 2013/154953). However, their approach requires a swept-source with multiple sweep speeds and a corresponding k-clock interferometer for each sweep speed for optimal use of detection bandwidth. Adding multiple k-clock interferometer options and synchronization increases the complexity of the system. And finally, this solution also requires a flexible rate swept source that may add complexity to the laser design. Everett et al. proposed the method to increase the A-scan rate of the system and have the option of multiple speeds, but the higher A-scan rate is achieved at the cost of reduction of axial resolution (U.S. Pat. No. 8,500,279).

To summarize, the solutions described in the prior art for multiple speed OCT operations add complexity or cost to the system. Specifications for detector electronics such as detection bandwidth, interferometer design to optimize reference power, and sweep rate of the laser are closely interlinked parameters that cannot be independently adjusted without impacting the optimized performance of the SS-OCT system. For example, for a given OCT imaging depth and unchanged axial resolution, the detection bandwidth will need to increase proportionally with an increase in the swept laser speed. In addition, reference power needs to be optimized for a given detector system to minimize the relative contribution of detector noise.

In SD-OCT systems, the reference optical power levels are typically optimized for reducing the noise contribution due to camera noise and autocorrelation artifacts. By increasing the reference power, the contribution due to detector noise is reduced relative to the photon shot noise, and the detection is described as shot noise dominated. While higher reference power is desired, it should not exceed the Full-Well Capacity (FWC) of the camera. In an SD-OCT system with a fixed reference power, if the camera exposure time is adjusted for various speeds, then the reference power would need to be optimized for the slowest operating speed to avoid camera saturation issue. This will lead to sub-optimal sensitivity performance at higher acquisition speeds. Alternatively, the sensitivity of multi-speed SD-OCT systems can be optimized by adjusting the reference arm power for different acquisition speeds to maintain fixed exposure energy on the camera per acquisition. However, such a design would increase the cost and complexity of the instrument.

In light of the above limitations, it would therefore be desirable for a single FD-OCT system (either SD-OCT or SS-OCT), to operate at multiple acquisition speeds with optimum sensitivity performance detection with minimal added complexity and system adjustments.

SUMMARY

The present application describes a Split Integration Mode (SIM) acqusition scheme that enables FD-OCT imaging at multiple rates without having to adjust the OCT interferometer reference arm attenuation to maintain optimum performance. This technique could be applied to either SD-OCT or SS-OCT systems. We define fundamental A-scan acquisition rate for a system as the maximum A-scan rate supported by a given system. Effective A-scan acquisition rates are the variable A-scan rates as generated by employing split integration mode (SIM). SIM mode enables an OCT system having a first mode and a second mode, wherein the fundamental acquisition rate of the detector is the same in the two modes, but wherein the generated signals in the second mode are digitally combined prior to signal processing to create a data set with an effective acquisition rate less than the fundamental acquisition rate.

In SD-OCT, SIM is achieved by always operating the camera at a fixed acquisition rate (or fundamental rate) corresponding to the maximum desired OCT acquisition rate, and operating at lower OCT rates by summing up sequential camera acquisitions signals in the digital domain (such as by use of field programmable gate arrays (FPGAs)). The data from the sequential camera acquisitions can be combined in multiple ways including summation of sprectral fringe data, summation of Fourier transform of spectral data, geometric mean of Fourier transform of spectral data etc. One of the key differentiating features of this mode of operation is that the camera acquisition rate is fixed for a single exposure, and hence the integration time of the camera is independent of the OCT data acquisition rate. Therefore the reference energy deposited on the camera per acquisition can be set to the optimum level, independent of the OCT acquisition rate. In comparison, if the camera exposure times were varied to set the OCT acquisition rate, as in a standard OCT system architecture, then reducing the OCT acquisition rate would result in saturation of the camera.

SIM makes it possible to operate a higher speed camera as if it were a lower speed camera, which is important for maintaining data compatibility between existing instruments and future SD-OCT systems equipped with high speed cameras. In one embodiment of the present application, different types of scans can be operated at different speeds using the same application software. For example, scans or applications requiring high data density including but not limited to OCT angiography, wide-field cube scans, and corneal topography can be acquired at the highest acquisition rate of the system. The scans or applications requiring higher SNR or back-compatibility with older legacy systems can be operated at effective lower speeds using the SIM approach.

In a preferred embodiment, at least two consecutive readouts are averaged or summed in the spectral domain before A-scan signal processing. It should be noted that the ratio of fundamental and effective A-scan acquisition rates may be a non-integer value value, if so desired. The processes can be performed at the firmware level where summation of combination of two or more consecutive spectra can be done electronically. Similarly, in SS-OCT system, SIM is achieved by always operating the swept laser and detection system corresponding to the maximum desired OCT acquisition rate (or fundamental OCT system rate), and operating at lower OCT rates by summing up at least two sequential interferometric spectral sweep signals in the digital domain (such as by use of field programmable gate arrays (FPGAs)). In one implementation of this embodiment, at least two consecutive interferometric spectral sweeps could be combined prior to A-scan signal processing, or information from the two consecutive sweeps could be used to generate a single A-scan.

DETAILED DESCRIPTION

Figure 1:
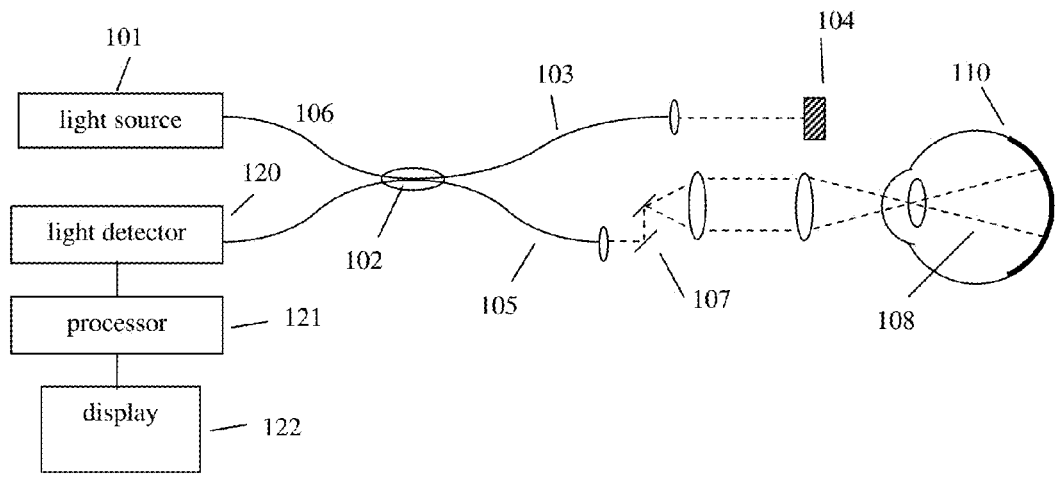
FIG. 1 illustrates a generalized FD-OCT system that can be operated in split integration mode (SIM).

A generalized FD-OCT system used to collect 3-D image data suitable for use with the present invention is illustrated in FIG. 1. A FD-OCT system includes a light source 101, typical sources including but not limited to broadband light sources with short temporal coherence lengths or swept laser sources. (See for example, Wojtkowski, et al., "Three-dimensional retinal imaging with high-speed ultrahigh-resolution optical coherence tomography," *Ophthalmology* 112(10):1734 2005 or Lee et al. "In vivo optical frequency domain imaging of human retina and choroid," *Optics Express* 14(10):4403 2006 the contents of both of which is hereby incorporated by reference).

Light from source 101 is routed, typically by optical fiber 106 through optical coupler 102 and though fiber 105, to illuminate the sample 110, a typical sample being tissues at the back of the human eye. While the retina is shown as the imaging target in FIG. 1, structures in other areas of the eye like the anterior chamber can also be imaged. The light is directed to the sample, typically with a pair of galvanometer scanners 107 between the output of the fiber and the sample, so that the beam of light can illuminate a series of transverse locations comprising the area on the eye to be imaged. Light scattered from the sample is collected, typically into the same fiber 105 used to route the light for illumination. Reference light derived from the same source 101 travels a separate path, in this case involving fiber 103 and retro-reflector 104. Those skilled in the art recognize that a transmissive reference path can also be used. The reference optical power levels are typically optimized for reducing the noise contribution due to camera or detector noise. By increasing the reference power, the contribution due to detector noise is reduced relative to the photon shot noise and the detection is described as shot noise dominated. Collected sample light is combined with reference light, typically in a fiber coupler 102, to form light interference in a detector 120. A typical detector for SD-OCT implementations is a spectrometer while a typical detector for SS-OCT implementations is a balanced detector. The output from the detector is supplied to a processor 121. The processor can generate images of the sample based on the output from the detector. The processing steps typically performed prior to image generation are discussed in further detail below. The resulting images can be stored in the processor or displayed on display 122. Additional measurements (e.g. layer thicknesses, areas, regions of pathology, etc.) can be made on the image data and can also be stored or displayed. The processing and storing functions may be localized within the OCT instrument or functions may be performed on an external processing unit to which the collected data is transferred. This unit could be dedicated to data processing or perform other tasks which are quite general and not dedicated to the OCT device.

The interference causes the intensity of the interfered light to vary across the spectrum. The spectral interference information from a given point is used to generate reflectivity depth profile information using a process called A-scan reconstruction. The processing is carried out in the processor as part of the image generation process. Typical processing steps of A-scan reconstruction include, but are not limited to, background reference light subtraction, dispersion correction, normalization, and inverse Fourier transform. The Fourier transform of the interference light, typically the last step in reconstruction process, reveals the profile of scattering intensities at different path lengths, and therefore scattering as a function of depth (typically referred to as z-direction) in the sample (see for example Leitgeb et al. "Ultrahigh resolution Fourier domain optical coherence tomography," *Optics Express* 12(10):2156 (2004) hereby incorporated by reference). The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path.

We now describe, split integration mode (SIM), a method of operating an OCT system wherein the A-scan acquisition rate of the system can be effectively changed with a minimum alteration of system parameters. We define the term fundamental A-scan acquisition rate as the maximum A-scan rate supported by the system. Effective A-scan acquisition rates are the variable A-scan rates generated by employing SIM. In an SD-OCT based system operating with this configuration, the camera is operated at the same acquisition rate for either mode, preferably the highest rate for the camera (or the fundamental A-scan acquisition rate), but the second mode has an apparent reduced acquisition rate created by digital combining of the collected data prior to further processing for reconstruction or image generation, referred to herein as SIM. As will be described in further detail below, this operating configuration is applicable to both SD-OCT and SS-OCT systems.

Figure 2:
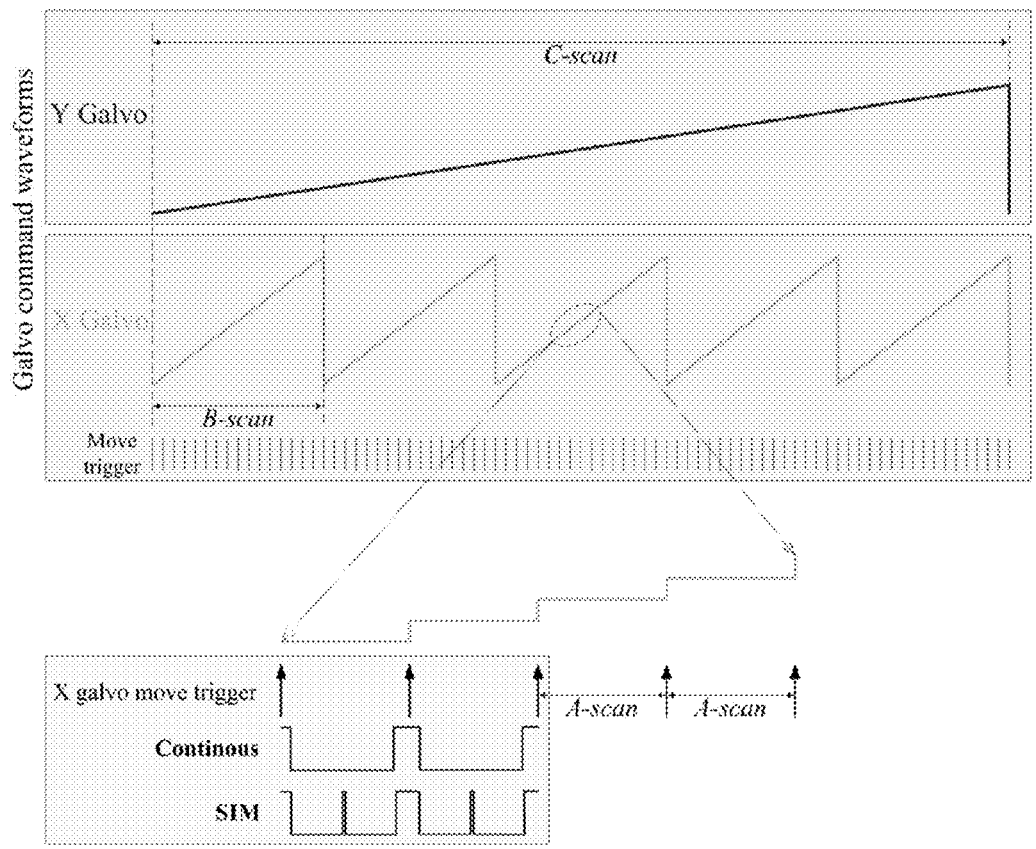
FIG. 2 illustrates the X and Y galvo waveforms used to collect a cube of SD-OCT data. The horizontal axis represents time. The circled region of the X-galvo waveform is expanded in the bottom view to illustrate A-scan data collection in continuous and SIM modes.

SIM enables more flexibility for the reference arm power. In one embodiment of the present application, the reference arm optical power level is adjusted such that the detector has a 70% filling factor (maximum spectral intensity reaching 70% of the camera saturation level) at its highest operation speed or the system fundamental A-scan acquisition rate (e.g. 67.5 kHz in a particular embodiment). This design yields minimal camera noise at the highest speed and the shot-noise dominated OCT acquisition can therefore be accomplished. With this setting and normal camera operation, if the camera was effectively operated at lower acquisition speeds (e.g. 27 kHz in a particular embodiment) the total integration time would be too long for this reference arm power level, and the camera would saturate (camera filling >100%). SIM overcomes the camera saturation limitation and maintains the imaging characteristics at lower speeds. As illustrated in FIG. 2, in SIM, imaging characteristics are maintained by splitting the A-scan integration time ($2t_i$) into multiple integration intervals with the same total duration ($t_i$ each for the case of two integration intervals). The overall SD-OCT timing diagram illustrated in FIG. 2 shows the difference between the continuous integration mode and SIM for the case of two integration intervals resulting in a factor of two reduction in the acquisition rates between the two modes. The top panel of FIG. 2 illustrates the command waveforms for the x and y galvanometer scanners responsible for scanning the OCT beam over the sample. On the bottom, a zoomed in image of a few A-scans is displayed. It should be noted that in this particular example, the ratio of the fundamental and effective A-scan acquisition rate is a non-integer value (67.5/27=2.5). In traditional continuous mode operation, the detector integrates over the entire A-scan acquisition time. In SIM mode, the integration time is split into multiple portions that are collected at a higher acquisition speed. When the readout time between the two shorter intervals approaches zero, the two acquisition modes are equivalent.

The information from two read-outs can be digitally combined in multiple ways. For example, the spectral interference from two readouts can be directly added at any stage prior to inverse Fourier transform step in the A-scan reconstruction process. There are several other approaches to combine the information from multiple readouts to effectively generate a single A-scan. Some of these approaches include, but are not limited to the following:

1. Adding the information from multiple readout measurements after the inverse Fourier transform step.

2. Adding the absolute value of the information from multiple readout measurements after the inverse Fourier transform step.
3. Adding the squared absolute value of the information from multiple readout measurements after the inverse Fourier transform step.
4. Obtaining the geometric mean of the squared absolute value of the information from multiple readout measurements after the inverse Fourier transform step.
5. Performing non-linear operations such as applying logarithmic functions to the absolute value of the information from multiple readout measurements and using various mathematical approaches to combine the outcome to produce a single output.

Figure 3:
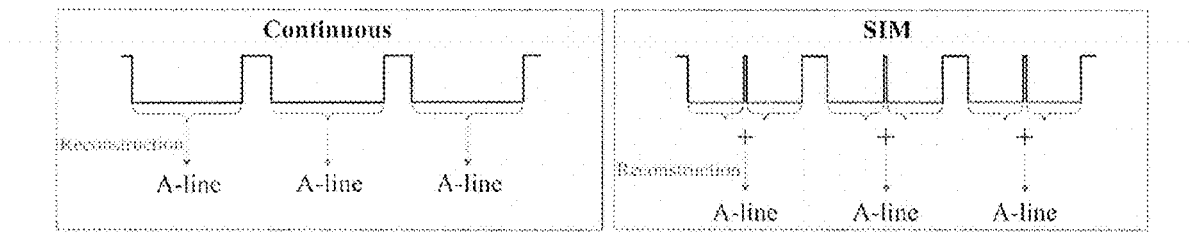
FIG. 3 displays how the raw signal is integrated in the camera pixels for each A-scan in continuous acqusition mode (left) whereas in SIM mode (right), the signal integration takes place in electrical circuitry.

In a preferred embodiment for the SD-OCT system, the readout of the two intervals is combined before A-line reconstruction. In continuous acquisition mode, light is integrated in the CCD pixels; whereas in SIM, integration of the readout signal is completed in the electrical circuitry. FIG. 3 compares the signal integration and processing steps in continuous mode (left) and SIM mode (right) to achieve the same apparent acquisition rate. The left side shows how raw signal is integrated within the camera pixels in standard continuous acquisition mode. The right side of FIG. 3 shows that integration in SIM mode is performed in the electrical circuitry before reconstructing the A-lines. In one embodiment of the invention, SIM integration is performed in the frame grabber's firmware. The same A-line reconstruction algorithms can be applied after integration.

Figure 4:
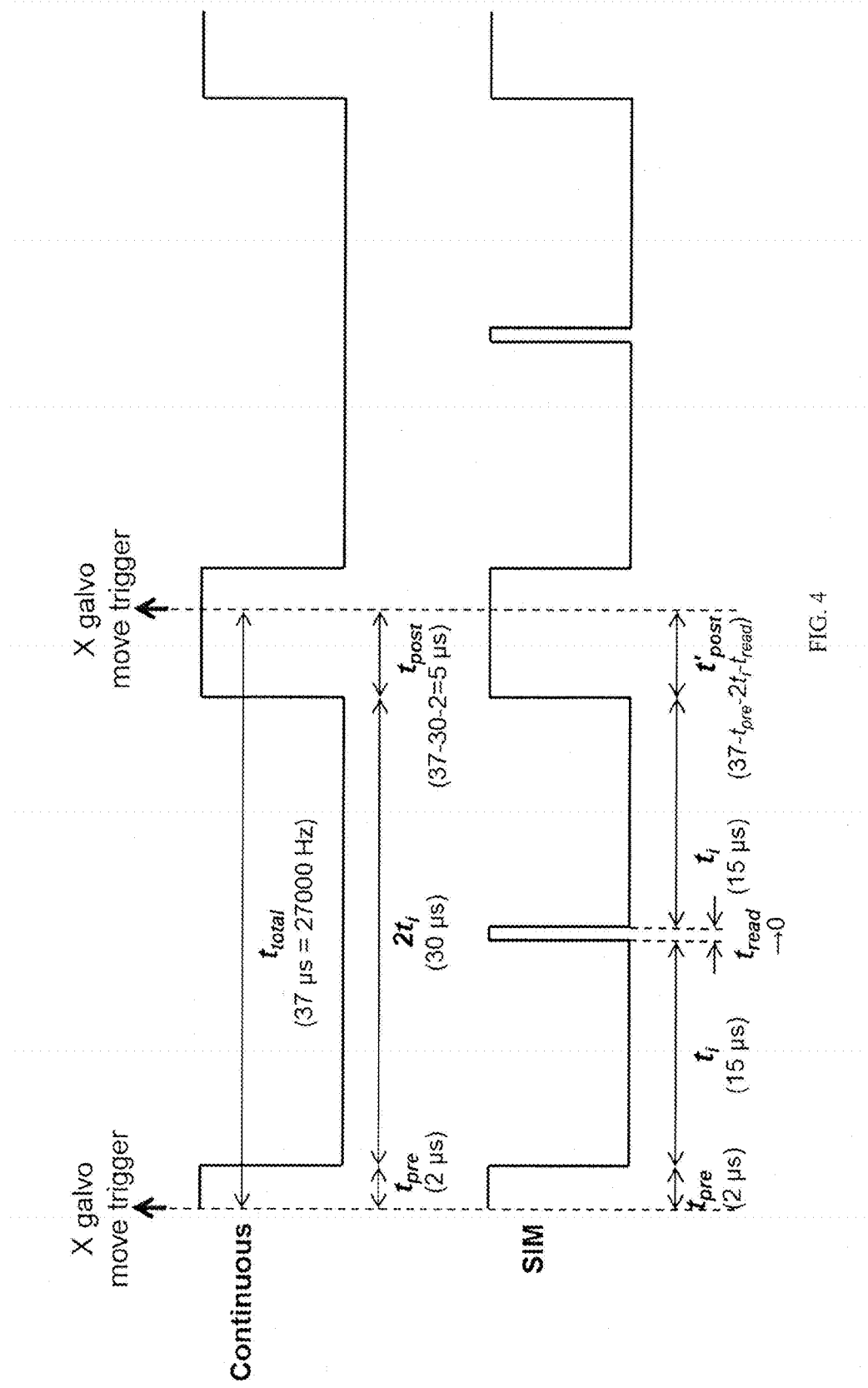
FIG. 4 illustrates the timing diagram for a specific embodiment of the present application in which SIM mode is used with a high speed camera (bottom) to maintain data compatibility with a system operating with a slower camera (top).

FIG. 4 shows the timing diagram for one specific embodiment, in which a SIM mode is established with a higher-speed camera to maintain compatibility with a legacy SD-OCT system running at a speed of 27 kHz with integration time of 30 µs. SIM integration intervals ($t_i$) can be set to 15 µs each, yielding a total integration time equal to the legacy system. The read-out time ($t_{read}$) is minimized to minimize any potential difference. Camera read-out is active when the command signal is low. This configuration has the potential to maintain data compatibility between the legacy normative database generated from the older system and the future SD-OCT system with the high-speed camera while still allowing the system to acquire scans at the high camera speed that are not necessarily compatible with legacy systems as will be discussed in further detail below. The reference arm optical power is set to have 70% camera filling when the continuous integration time is about 14.8 µs; which corresponds to 67.5 kHz acquisition speed. This configuration will enable shot-noise-dominated detection at the two acquisition speeds without changing the reference arm power.

Figure 5:
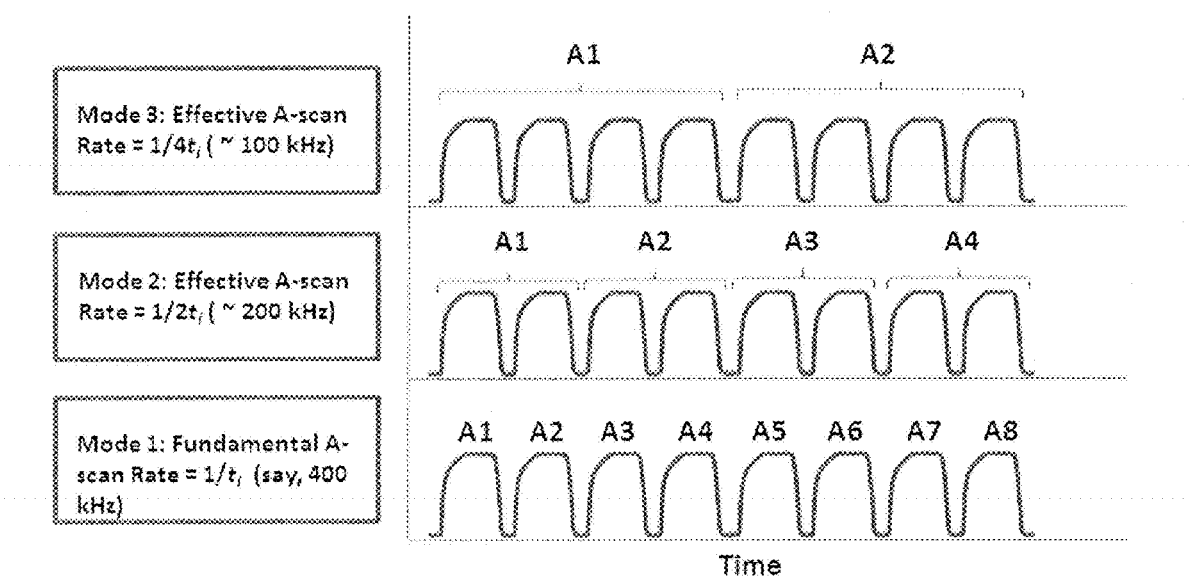
FIG. 5 is a schematic timing diagram showing an example for SIM implementation in an SS-OCT embodiment to obtain 3 OCT acquisition modes. Mode 1 is the fundamental mode. In Mode 2, information from two consecutive sweeps are used to generate a single A-scan. In Mode 3, information from four consecutive sweeps are used to generate a single A-scan.

In an alternate embodiment for the SS-OCT system, the system hardware including the interferometer, detection system, reference power levels etc. can be optimized for the maximum or fundamental sweep rate of the wavelength sweeping source. Operation at lower effective A-scan rates can be realized by use SIM approach of digitally summing up at least two sequential interferometric spectral sweep signals (such as by use of FPGA, DSP etc.). The two consecutive interferometric spectral sweeps could be combined prior to A-scan signal processing, or information from the two consecutive sweeps could be used to generate a single A-scan, thereby reducing the effective A-scan rate by at least a factor of two. One of the primary advantage of this approach is that the swept laser need not operate at multiple speeds, thereby significantly simplifying the system design complexity and reducing cost. FIG. 5. shows one such example where an SS-OCT system can operate at up to 3 different effective A-scan rate s using the SIM approach. The fundamental mode (Mode 1) operates at the highest rate, corresponding to the optimized fixed sweep rate of the laser source in this figure, 400 KHz. In Mode 2, information from two consecutive sweeps are used to generate a single A-scan and the system operates at half the fundamental A-scan rate (200 KHz). In Mode 3, information from four consecutive sweeps are used to generate a single A-scan and the system operates at a quarter of the fundamental A-scan rate (100 Khz).

SIM mode makes it possible for different types of scans to be operated at different speeds using the same application software. For example, scans or applications requiring high data density including but not limited to OCT angiography, wide-field cube scans, high resolution zoom cubes, and corneal topography can be acquired at the highest acquisition rate of the system. Applications such as OCT angiography and corneal topography or corneal power calculations would benefit from faster acquisition speeds as the effect of motion related artifacts can be suppressed at higher speed. In OCT angiography, measurements such as A-scans or B-scans are repeated at approximately the same location and used to generate motion contrast signal for detection of blood flow etc. Precise correction for the motion between such multiple measurements is a key factor to improve the accuracy of generating motion contrast information. Post-processing motion correction approaches are either less effective or very time consuming if such corrections are made for slower speed systems. Hence in most applications of OCT angiography, it would be beneficial to choose the highest possible acquisition rate (fundamental acquisition rate) of the system. Wide field cube scans would also benefit from higher speed as larger FOV regions can be imaged in the eye in the same acquisition time. In another application that may benefit from faster speed, the spatial sampling of acquired data points could be increased if the FOV and the acquisition time remains the same. High resolution cubes may find use in obtaining more detailed high resolution information about the structural changes caused by a given pathology.

The scans or applications requiring higher SNR or back-compatibility with older legacy systems can be operated at effective lower speeds using the SIM approach. For example, if there is a need to visualize structures in the eye such as vitreous or deeper choroids, it may be desired to operate the system in the second mode that operates at an effectively lower acquisition rates but is capable of generating higher SNR images.

Although various applications and embodiments that incorporate the teachings of the present invention have been shown and described in detail herein, those skilled in the art can readily devise other varied embodiments that still incorporate these teachings.

The following references are hereby incorporated by reference:

PATENT DOCUMENTS

PCT Publication WO 2013/154953
U.S. Pat. No. 8,500,279
U.S. Pat. No. 8,504,141
US Patent Publication No. 2013/0120757

NON-PATENT LITERATURE

B. Potsaid et al., "Ultrahigh Speed Spectral/Fourier domain OCT Ophthalmic Imaging at 70,000 to 312,500 axial scans per second," Optics Express, 16 (19), pp 15149-15169 (2008)

B. Potsaid et al., "MEMS tunable VCSEL light source for ultrahigh speed 60 kHz-1 MHz axial scan rate and long range centimeter class OCT imaging," SPIE Proceedings, 8213, 82130M-1 (2012)

Nassif et al., "In vivo high-resolution video-rate SD-OCT of the human retina and optic nerve," Optics Express, 12 (3), pp 367-376 (2004)

S. H. Yun, G. J. Tearney, J. F. deBoer, and B. E. Bouma, "Motion artifacts in optical coherence tomography with frequency-domain ranging," Optics Express, 12, pp 2977-2998 (2004).

R. Leitgeb, C. K. Hitzenberger, and A. F. Fercher, "Performance of Fourier domain vs time domain optical coherence tomography," Optics Express, 11, pp 889-894 (2003).

Huang et al. "Optical Coherence Tomography" Science 254 (5035):1178 1991.

Leitgeb et al. "Ultrahigh resolution Fourier domain optical coherence tomography," Optics Express 12(10):2156 (2004)

Wojtkowski, et al., "Three-dimensional retinal imaging with high-speed ultrahigh-resolution optical coherence tomography," *Ophthalmology* 112(10):1734 2005 Lee et al. "In vivo optical frequency domain imaging of human retina and choroid," *Optics Express* 14(10):4403 2006

The invention claimed is:

1. An optical coherence tomography (OCT) system for imaging a sample, said system comprising:
   a light source for generating a beam of radiation;
   a beam divider for separating the beam of radiation into a sample arm and a reference arm;
   optics for scanning the beam in the sample arm over a set of transverse locations on the sample;
   a detector for measuring light returned from both the sample arm and the reference arm at a fundamental acquisition rate and generating signals in response thereto; and
   a processor for processing the signals and generating images of the sample based on the processed signals,
   said OCT system capable of having a first mode and a second mode, wherein the fundamental acquisition rate of the detector is the same in the two modes, but wherein the generated signals in the second mode are digitally combined prior to signal processing to create a data set with an effective acquisition rate less than the fundamental acquisition rate.

2. An OCT system as recited in claim 1, wherein the light source is a swept laser source.

3. An OCT systems as recited in claim 1, wherein the detector is a spectrometer comprising a pixel array and wherein the fundamental acquisition rate is determined by the integration time of the pixel array.

4. An OCT system as recited in claim 3, wherein the integration time in the second mode comprises two or more intervals, said intervals being combined digitally after acquisition to create the data set with an effective acquisition rate less than the fundamental acquisition rate.

5. An OCT system as recited in claim 4, wherein the fundamental acquisition rate is 67.5 KHz and the effective acquisition rate is 27 KHz.

6. An OCT system as recited in claim 1, wherein the first mode is used to generate high resolution images of the sample and the second mode is used to generate high SNR images of the sample.

7. An OCT system as recited in claim 1, wherein the effective acquisition rate is selected to create data compatible with a legacy system.

8. A method of collecting optical coherence tomography imaging data of a sample, said method comprising:
   scanning a beam of radiation over a first series of transverse locations on the sample;
   detecting combined light returning from the sample and light from a reference arm at a fundamental acquisition rate;
   deriving signals from the detected light to form a first data set;
   processing the signals in said first data set to generate a first image of the sample;
   scanning a beam of radiation over a second series of transverse locations on the sample;
   detecting combined light returning from the sample and light from a reference arm at the fundamental acquisition rate;
   deriving signals from the detected light to form a second data set;
   digitally combining the signals in the second data set before further processing to create a third data set wherein the third data set has an effective acquisition rate that is less than the fundamental acquisition rate;
   processing the signals in said third data set to generate a second image of the sample;
   storing or displaying the first and second images or measurements made therefrom.

9. A method as recited in claim 8, wherein the beam of radiation is generated from a light source that is swept in frequency.

10. A method as recited in claim 8, wherein the detected light is collected using a spectrometer comprising a pixel array and wherein the fundamental acquisition rate is determined by the integration time of the pixel array.

11. A method as recited in claim 10, wherein the digital combining occurs before the processing step.

12. A method as recited in claim 8, wherein the first and second series of transverse locations are the same.

13. A method as recited in claim 12, wherein the first and second data sets are the same.

14. A method as recited in claim 8, wherein the effective acquisition rate is selected to maintain data compatibility with a legacy OCT system.

15. An OCT system as recited in claim 8, wherein the first image is a high resolution image of the sample and the second image is a high SNR image of the sample.

* * * * *